United States Patent
Ido et al.

(10) Patent No.: US 7,284,445 B2
(45) Date of Patent: Oct. 23, 2007

(54) STRAIN WAVEFORM CONTROL APPARATUS, STRAIN WAVEFORM REGULATING MEMBER, STRAIN WAVEFORM CONTROL METHOD BY USING STRAIN WAVEFORM CONTROL APPARATUS, AND STRAIN WAVEFORM CONTROL PROGRAM

(75) Inventors: Osamu Ido, Kawasaki (JP); Tadashi Tateno, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 11/022,777

(22) Filed: Dec. 28, 2004

(65) Prior Publication Data

US 2005/0115332 A1 Jun. 2, 2005

Related U.S. Application Data

(63) Continuation of application No. PCT/JP02/09752, filed on Sep. 24, 2002.

(30) Foreign Application Priority Data

Sep. 24, 2002 (JP) .................. PCT/JP02/09752

(51) Int. Cl.
G01N 29/04 (2006.01)

(52) U.S. Cl. ..................................... 73/801

(58) Field of Classification Search ............ 73/801, 73/12.01, 862, 46, 12.05, 770; 702/106
See application file for complete search history.

(56) References Cited

U.S. PATENT DOCUMENTS

| | | | | |
|---|---|---|---|---|
| 3,924,456 A | * | 12/1975 | Vahaviolos | 73/770 |
| 4,579,003 A | * | 4/1986 | Riley | 73/784 |
| 4,869,175 A | * | 9/1989 | McDougal | 102/518 |
| 4,896,339 A | * | 1/1990 | Fukumoto | 377/19 |
| 5,024,091 A | * | 6/1991 | Pellerin et al. | 73/597 |
| 5,101,162 A | * | 3/1992 | Webster et al. | 324/618 |
| 5,487,298 A | * | 1/1996 | Davis et al. | 73/12.05 |
| 5,606,515 A | * | 2/1997 | Mockapetris et al. | 702/106 |
| 6,389,876 B1 | * | 5/2002 | Tanimura et al. | 73/12.01 |
| 6,836,093 B1 | * | 12/2004 | Nishi | 318/649 |

FOREIGN PATENT DOCUMENTS

| JP | 62-298739 | 12/1987 |
|---|---|---|
| JP | 10-090110 | 4/1998 |

* cited by examiner

Primary Examiner—Michael Cygan
Assistant Examiner—Octavia Davis
(74) Attorney, Agent, or Firm—Staas & Halsey LLP

(57) ABSTRACT

A strain waveform control apparatus of the present invention is adapted to horizontally supporting a printed circuit board over a trestle and cause strains on the printed circuit board by a dropped rigid ball with buffer blocks being located on both surfaces of the printed circuit board. These buffer blocks are movably supported by movable stages so as to be in contact with proper places of both surfaces of the printed circuit board. The buffer blocks are capable of regulating and relatively modify/adjusting first and second occurred strain waveforms generated by application of the impact to the printed circuit board and modifying/adjusting a steepness of each of the strain waveforms.

39 Claims, 8 Drawing Sheets

STRAIN WAVEFORM CONTROL APPARATUS, STRAIN WAVEFORM REGULATING MEMBER, STRAIN WAVEFORM CONTROL METHOD BY USING STRAIN WAVEFORM CONTROL APPARATUS, AND STRAIN WAVEFORM CONTROL PROGRAM

This application is a continuing application, filed under 35 U.S.C. §111(a), of International Application PCT/JP02/09752, filed Sep. 24, 2002.

BACKGROUND OF THE INVENTION

1. Field of the Invention

The present invention relates to a strain waveform control apparatus adapted to support a strain waveform regulating member to bring it into contact with a proper place of a fixedly-supported specimen and generate strain waveforms by applying an impact to the specimen and then control (modify and adjust) strain waveforms, and further relates to the strain waveform regulating member, a strain waveform control method by using the strain waveform control apparatus and a strain waveform control program. In particular, the present invention relates to a strength evaluation using an impact test device (inclusive of a destructive test device) by generating any strains on a printed circuit board in the neighborhood of a micro junction part such as a solder junction part formed in an electronic component and a conductive pattern adhesion part formed on its circuit board, respectively.

2. Description of the Related Art

The conventional impact test device is configured to generate strains on a printed circuit board fixed in place by applying an impact force thereto. The strain waveforms generated on the printed circuit board are determined by an initial impact force and/or a fixing position for the printed circuit board. The impact test device is also configured to control a vibration appearing on the strain waveforms by changing the impact force and particularly to limit an object to be controlled only to an initially generated strain.

For example, in Japanese Laid-Open patent publication No. 62-298739, there is described a apparatus adapted to verify an integrity of a solder joint part between a lead line of a IC-package and a printed wiring on a IC-package mounted printed circuit board.

However, even if a test of a printed circuit board is performed by externally application of an impact force thereto on the condition that the printed circuit board is simply fixed in place, it is often difficult to regard the printed circuit board as a final product and evaluate it because the result obtained from such a test (for example, a damping factor of a strain peak is generally apt to be constant) is different from that obtained when the printed circuit board has actually been built in a box-like body, e.g., an outer casing, as the final product. Therefore, even if the impact test is performed in a state as possible as near to a final product, it is disadvantageously impossible for the conventional impact test device to control a shape(s) of a strain waveform(s) (particularly, first and second occurred waveforms) generated by a damping vibration occurred with the impact into a desired shape(s). For example, when a bigger impact is applied to a specimen in order to prevent a peak of the second occurred waveform from being lessened so much, only a peak of the first occurred waveform (the maximum strain waveform peak) is enlarged because of the phenomenon that the specimen will expand depending on the impact without much change in the second occurred waveform peak. Accordingly, it is disadvantageously often difficult to enlarge relatively the second occurred strain waveform peak than the first occurred strain waveform peak by using the same specimen. On the contrary, when it is intended to lessen only the second occurred strain waveform peak relatively in comparison with the first occurred strain waveform peak, the first occurred strain waveform peak is also lessened in addition to the second occurred strain waveform peak. Thus, it is disadvantageously often difficult to lessen only the second occurred strain waveform peak.

SUMMARY OF THE INVENTION

The prevent invention is accomplished by dissolving these problems as described above. Thus, an object of the present invention is to provide a strain waveform control apparatus that is adapted to control (modify/adjust) strain waveforms obtained by applying an impact to a specimen, e.g., to control (modify/adjust) a shape of each of first and second occurred strain waveforms by regulating peaks of the strain waveforms, and further adapted to control (modify/adjust) a steepness of each of the strain waveforms. The present invention further provides a strain waveform regulating member for use in the strain waveform control apparatus, a strain waveform control method by using the strain waveform control apparatus and a strain waveform control program.

According to an aspect of the present invention, there is provided a strain waveform control apparatus, comprising:
a specimen supporting portion adapted to support a specimen at a proper location of the specimen;
a strain generating portion adapted to generate strains by applying an impact to the specimen supported by the specimen supporting portion;
a strain waveform detecting portion adapted to detect strain waveforms of the specimen generated by the strain waveform generating portion;
at least one strain regulating member adapted to be contactably located on a proper place of a strain-causing surface of the specimen; and
a strain regulating member supporting portion adapted to movably support the at least one strain regulating member.

This strain waveform control apparatus according to the present invention can be applicable to an impact test device inclusive of a destructive test device. The specimen comprises, for example, a printed circuit board, mobile equipments, PC and the like. The strain generating portion may be a device of a rigid ball drop-type, of a hammer-type to hit the specimen by a hammer, or a striking bar-type to strike the specimen. The strain waveform detecting portion may be, for example, a combination of a strain gauge adapted to convert strains into electrical signals and a dynamic strain meter adapted to measure strain waveforms from electrical signals of the strain gauge. An embodiment of the strain regulating member will be explained as a buffer block in the following description. Also, an embodiment of the strain regulating member supporting portion will be explained as a movable stage in the following description.

Also, the strain waveform control apparatus according to the present invention further comprises a control portion adapted to drive the strain regulating member supporting portion to move the at least one strain regulating member so as to change strain waveforms detected by the strain waveform detecting portion into predetermined waveforms. For example, an embodiment of this control portion may be comprised of a personal computer (PC).

In particular, the control portion of the strain waveform control apparatus according to the present invention is capable of controlling a positional relationship between the at least one strain regulating member and the specimen by driving the strain regulating member supporting portion so as to confine a first peak of strain waveforms generated by the impact within a predetermined range.

Also, the control portion of the strain waveform control apparatus according to the present invention is capable of controlling a positional relationship between the at least one strain regulating member and the specimen by driving the strain regulating member supporting portion so as to confine a second peak of strain waveforms generated by the impact within a predetermined range.

Further, the control portion of the strain waveform control apparatus according to the present invention is capable of controlling a positional relationship between the at least one strain regulating member and the specimen by driving the strain regulating member supporting portion so as to confine the maximum peak of strain waveforms generated by the impact within a predetermined range.

Yet further, the control portion of the strain waveform control apparatus according to the present invention is capable of controlling a positional relationship between the at least one strain regulating member and the specimen by driving the strain regulating member supporting portion so as to confine the second largest peak of strain waveforms generated by the impact within a predetermined range.

Still further, the control portion of the strain waveform control apparatus according to the present invention is capable of controlling a positional relationship between the at least one strain regulating member and the specimen by driving the strain regulating member supporting portion so as to confine a steepness of each of strain waveforms generated by the impact within a predetermined range.

Also, the control portion of the strain waveform control apparatus according to the present invention is capable of controlling a positional relationship between the at least one strain regulating member and the specimen by driving the strain regulating member supporting portion so as to relatively modify/adjust first and second occurred waveforms of strain waveforms generated by the impact.

Also, in the strain waveform control apparatus, the strain regulating member supporting portion is capable of supporting the at least one strain regulating member so as to be movable in a direction perpendicular to an impacted surface of the specimen.

Also, in the strain waveform control apparatus, the strain regulating member supporting portion is capable of supporting the at least one strain regulating member so as to be movable in a direction parallel to an impacted surface of the specimen.

Also, in the strain waveform control apparatus, the strain regulating member supporting portion is capable of supporting the strain regulating member in a face-to-face relation to an impacted surface of the specimen and supporting the other strain regulating member in a face-to-face relation to the opposite surface of the specimen.

In particular, in the strain waveform control apparatus, the at least one strain regulating member comprises: a first (main) strain regulating member being effective in changing the magnitude of each of peaks of the strain waveforms; and a second (auxiliary) strain regulating member being effective in changing a steepness of each of peaks of the strain waveforms.

Also, in the strain waveform control apparatus, the specimen comprises a printed circuit board.

According to another aspect of the present invention, there is provided a strain waveform control apparatus, comprising:

a specimen supporting portion adapted to support a specimen at a proper location of the specimen;

a strain generating portion adapted to generate strains by applying an impact to the specimen supported by the specimen supporting portion;

a strain waveform detecting portion adapted to detect strain waveforms of the specimen generated by the strain waveform generating portion; and a strain regulating member supporting portion adapted to movably support at least one strain regulating member to locate it contactably on and in a face-to-face relation to a proper place of a strain-causing surface of the specimen.

In particular, the at least one strain regulating member which can be supported by the strain regulating member supporting portion in the strain waveform control apparatus comprises a plurality of strain regulating members.

Also, the at least one strain regulating member has a predetermined elastic modulus.

In the event that the at least one strain regulating member has a predetermined elastic modulus, the at least one strain regulating member can be composed of a rubber material. Or, the at least one strain regulating member, particularly its part which is supported by the strain regulating member supporting portion, can be composed of a spring material. Additionally, the at least one strain regulating member, particularly its part which can be in contact with a surface of the specimen, composed of a rubber material. Also, in the at least one strain regulating member, the spring material part is independently exchangeable for others.

According to a further aspect of the present invention, there is provided a strain waveform control apparatus equipped for an impact test device which is adapted to apply an impact to a specimen, comprising:

a strain regulating member adapted to be contactably located on a proper place of a strain causing surface of the specimen and regulate strains generated on the specimen; and a strain regulating member supporting/transporting mechanism attached to a proper location of the impact test device and adapted to support the strain regulating member so as to be movable in a direction perpendicular and in a direction parallel to the strain causing surface of the specimen.

The strain waveform control apparatus according to the present invention further comprises a control portion adapted to drive the strain regulating member supporting/transporting mechanism to control a position of the strain regulating member.

According to a still further aspect of the present invention, there is provided a method of controlling strain waveforms by using a strain waveform control apparatus adapted to support a specimen at a proper location of the specimen and to support a strain regulating member to be contactably located on a proper place of the specimen, and further adapted to apply an impact to the specimen so as to generate strain waveforms and yet further adapted to control the strain waveforms, comprising the steps of:

(a) detecting the strain waveforms generated by application of the impact to the specimen; and (b) changing a position of the strain regulating member based on the strain waveforms detected in the step of detecting the strain waveforms and controlling the strain waveforms to be converted into predetermined strain waveforms.

In particular, the step (b) comprises moving the strain regulating member so as to confine a first peak of strain waveforms generated by the impact within a predetermined range. Also, the step (b) comprises moving the strain regulating member so as to confine a second peak of strain waveforms generated by the impact within a predetermined range. Further, the step (b) comprises moving the strain regulating member so as to confine the maximum peak of strain waveforms generated by the impact within a predetermined range. Furthermore, the step (b) comprises moving the strain regulating member so as to confine the second largest peak of strain waveforms generated by the impact within a predetermined range. Yet further, the step (b) comprises moving the strain regulating member so as to confine a steepness of each of strain waveforms generated by the impact within a predetermined range. Also, the step (b) comprises moving the strain regulating member adapted to relatively modify/adjust first and second occurred waveforms of strain waveforms generated by the impact.

According to a yet further aspect of the present invention, there is provided a program adapted to cause a computer to execute a strain waveform control in a strain waveform control apparatus adapted to support a specimen at a proper location of the specimen and to support a strain regulating member to be contactably located on a proper place of the specimen, and further adapted to apply an impact to the specimen so as to generate strain waveforms and control the strain waveforms, the program comprising the steps of:

(a) detecting the strain waveforms generated by application of the impact to the specimen; and (b) changing a position of the strain regulating member based on the strain waveforms detected in the step of detecting the strain waveforms and controlling the strain waveforms to be converted into predetermined strain waveforms.

In particular, the step (b) of the program comprises moving the strain regulating member so as to confine a first peak of strain waveforms generated by the impact within a predetermined range. Or, the step (b) of the program comprises moving the strain regulating member so as to confine a second peak of strain waveforms generated by the impact within a predetermined range. Or, the step (b) of the program comprises moving the strain regulating member so as to confine the maximum peak of strain waveforms generated by the impact within a predetermined range. Or, the step (b) of the program comprises moving the strain regulating member so as to confine the second largest peak of strain waveforms generated by the impact within a predetermined range. Or, the step (b) of the program comprises moving the strain regulating member so as to confine a steepness of each of strain waveforms generated by the impact within a predetermined range. Or, the step (b) of the program comprises changing a position of the strain regulating member adapted to relatively modify/adjust first and second occurred waveforms of strain waveforms generated by the impact.

In addition, the strain control program according to the present invention can be stored in a computer-readable storage medium. The computer-readable medium may comprise any one of a CD-ROM, a flexible disk (FD), a DVD disk, an opto-magnetic disk, a portable storage medium such as an IC card and the like, a database storing computer programs, the other computer or its database.

PREFERRED EMBODIMENTS OF THE PRESENT INVENTION

Hereinafter, preferred embodiments of the present invention will be described in detail with reference to the accompanying drawings.

First Embodiment

Figure 1:
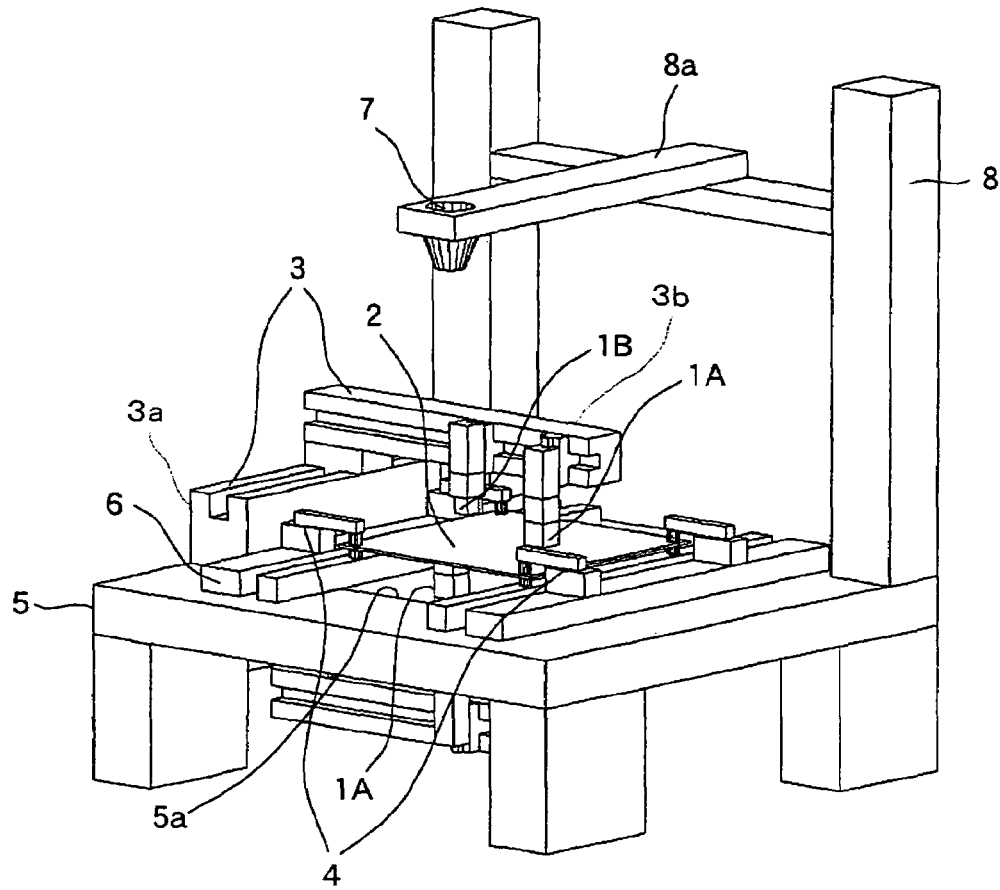
FIG. 1 is an external perspective view showing a rigid ball drop-type impact test device according to a first embodiment of the present invention.

FIG. 1 is an external perspective view showing a rigid ball drop-type impact test device according to a first embodiment of the present invention. In this impact test device, there is provided a predetermined printed circuit board setting part 4 provided on a printed circuit board supporting mount 6 on a trestle 5. On this printed circuit board setting part 4, there is a printed circuit board 2 as a specimen gripped at its peripheral proper locations by pressing its opposite sides. In the embodiment as shown in FIG. 1, four corners of the quadrangle printed circuit board 2 are gripped respectively by four printed circuit board setting parts 4 provided on the printed circuit board supporting mount 6. For example, the printed circuit board 2 has a size of 110 mm□×0.8 mm and may be a specimen sample implementing on its center a BGA (Ball Grid Allay) package.

On upper and lower surfaces (front and rear surfaces) of the printed circuit board 2, there are provided two buffer blocks 1A, 1B as strain waveform regulating members. Each of the buffer blocks 1A, 1B is supported by its corresponding movable stage 3 and capable of coming in contact with and moving on its corresponding surface of the printed circuit board 2. These buffer blocks 1A, 1B are comprised of a main buffer block 1A serving to mainly regulate a peak size of a strain waveform and an auxiliary buffer block 1B serving to regulate a peak rising of a strain waveform (steepness), which are each movable in a direction parallel and perpendicular to the front or rear surface of the printed circuit board in a fixed state. In particular, these buffer blocks 1A, 1B are located to be in contact with or slightly distant from the surfaces of the printed circuit board 2. The movable stages 3 are provided respectively at upper and lower sides of the trestle 5. For example, the upper-sided movable stage 3 includes a first stage 3a provided on one lateral side of the printed circuit board supporting mount 6 and a second stage 3b which is movable along the first stage 3a and supports the main or auxiliary buffer blocks 1A, 1B so as to move it in a direction perpendicular to the former movable direction. Similarly, another set of first and second stages 3a, 3b having identical constructions to the aforementioned first and second stages 3a, 3b are also provided at the lower side of the trestle 5 such that another set of buffer blocks 1A, 1B can appropriately come in contact with and movable along the rear surface of the printed circuit board 2.

In particular, the buffer blocks 1A, 1B provided at the lower side of the trestle 5 is capable of being in contact with the rear surface of the printed circuit board 2 through an opening 5a perforated at a center of the trestle 5 (at the lower surface of the printed circuit board 2).

These movable stages 3 and the buffer blocks 1A, 1B connected to the former are configured to be attachable and unattachable as one set to the trestle 5, e.g., attachable and unattachable as one set to a trestle of the existing impact test device.

Figure 5:
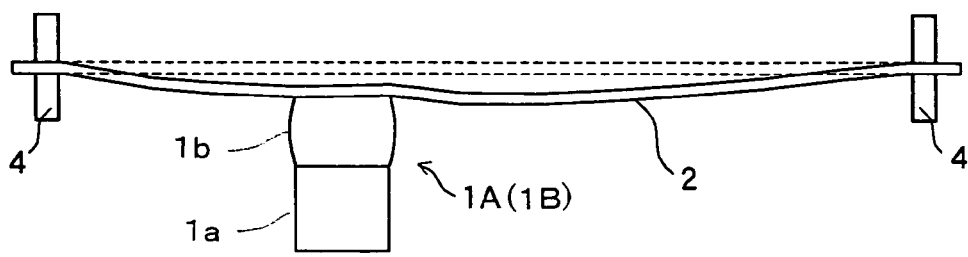
FIG. 5 is a schematic diagram showing an action of the strain waveform control apparatus.

As shown in FIG. 5, when a strain is occurred on the printed circuit board 2 so as to cause it to be curved, the buffer block 1A (1B) is configured to come in contact with (or abut) on a proper place of a protruded surface due to the curvature in order to regulate the strain and to modify/adjust the strain waveforms (it is referred as to a "strain waveform control" hereinafter in this specification). More specifically, these buffer blocks are located to be in contact with the front and rear surfaces of the printed circuit board or neighborhoods of the surfaces of the printed circuit board when the printed circuit board undergoes the strain such that it is curved.

Figure 12:
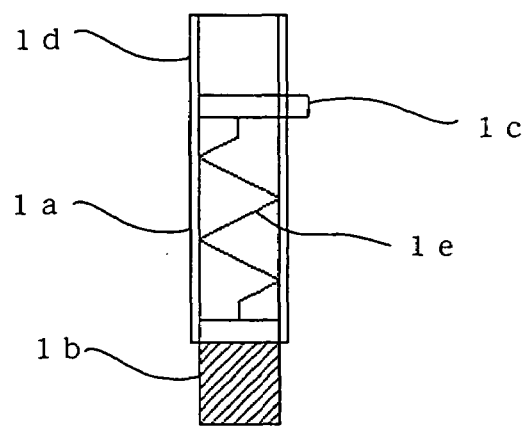
FIG. 12 is a side sectional view showing an example of butter blocks.

Further, each of these buffer blocks 1A, 1B is comprised of a supporting part 1a which is supported by the movable stage and a contacting part 1b which comes in contact with its corresponding surface of the printed circuit board. This contacting part 1b is preferably composed of a rubber material but may be composed of another material, e.g., plastics and any metal such as aluminum, which will not blemish the printed circuit board. Such a buffer member may be composed of the rubber material as mentioned above together with an elastic material having a predetermined elastic modulus (spring coefficient), or composed of an elastic material having a predetermined elastic modulus instead of the rubber material. In that case, it may be possible to maintain a predetermined elastic modulus in a contact (press) direction of the buffer block onto the printed circuit board. For example, as shown in FIG. 12, it may be possible that the supporting part 1a is composed of a spring material while the contacting part 1b is composed of the rubber material. Specifically, the supporting part 1a includes a cylindrical casing 1d in which the spring material (coil spring) 1e is inserted as shown in FIG. 12. In the cylindrical casing 1d, there is provided a spring setting part 1c which is attached to a proximal end side of the cylindrical casing 1d and to which the spring material 1e is connected at its one end. Thus, the contacting part (rubber material) 1b is inserted in a distal end side of the cylindrical casing 1d and elastically supported by the other end of the spring material 1e with the predetermined spring coefficient. In particular, the coil spring as the spring material may be another kind of spring material such as a leaf spring.

In the event that there are prepared many kinds of buffer blocks having different spring coefficients (elastic moduli) as the auxiliary buffer blocks 1B, any one of such buffer blocks 1B can be selected as a replacement with respect to the movable stage 3. Therefore, if the event that the auxiliary buffer block is comprised of the supporting part 1a made of a spring material and the contacting part 1b, it is possible to replace only the supporting part 1a with another supporting part having a different spring coefficient. The supporting part can be connected to the contacting part by screws or an elastic material and the like. In this embodiment, a contact area by which each of the buffer blocks 1A, 1B is in contact with the printed circuit board is set to 10 mm□. However, if such a contact area changes, a changing amount of the strain waveforms also changes. Needless to say, it is possible to perform a higher freedom control by relatively reducing the contact area of the buffer blocks to the printed circuit board and by increasing the number of the buffer blocks.

In this embodiment, the main buffer block 1A is provided at a distal end of the second movable stage 3b while the auxiliary buffer block 1B is provided at a proximal end thereof, but vice versa is possible. Also, the auxiliary buffer block 1B may be configured to be movable separately and independently from the main buffer block 1A. These movable stages moves the buffer blocks 1A, 1B by a transport mechanism, e.g., utilizing a rack-and-pinion.

Figure 10:
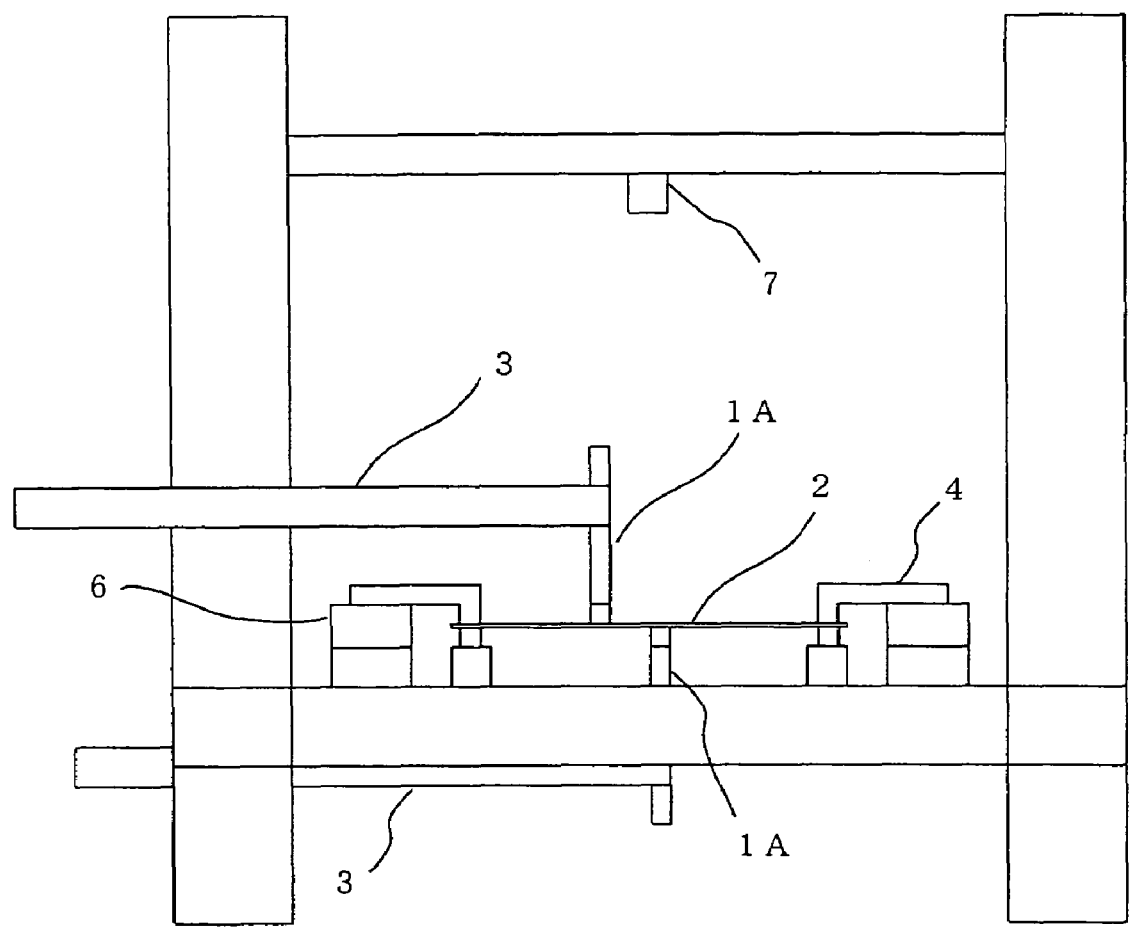
FIG. 10 is a side view showing other embodiment of the impact test device than that of FIG. 1.

Further, these buffer blocks are arranged, as described above, to locate the main buffer block 1A on the upper surface of the printed circuit board 2 and locate the auxiliary buffer block 1B on the lower surface of the printed circuit board 2. However, the present invention can be achieved to perform a peak control of the strain waveforms by utilizing only the main buffer block 1A without the provision of the auxiliary buffer block 1B, as shown in FIG. 10. More specifically, it is possible to control a peak of the strain waveform and its rising (steepness) only by the main buffer block 1A, but their controls can be performed with a greater freedom by utilizing the auxiliary buffer block 1B in addition to the main buffer block 1A. According to the present invention, there is no problem in the case where both of the main and auxiliary buffer blocks 1A, 1B are provided only on the lower surface of the printed circuit board 2 while the main buffer block 1A is provided only on the upper surface of the printed circuit board 2, and vice versa is possible. Also, according to the present invention, there is no problem in the case where a plurality of the main and auxiliary buffer blocks 1A, 1B are provided on the upper and lower surfaces of the printed circuit board 2. In particular, when it is intended to regulate the strain waveforms occurred only on one surface of the printed circuit board, the main and/or auxiliary buffer block(s) 1A, 1B may be provided on that one surface only. For example, when it is intended to regulate a first occurred strain waveform peak, the main and auxiliary buffer blocks 1A, 1B may be provided only on a rear side (opposite surface to a surface to which an impact is applied) of the printed circuit board 2.

Returning to FIG. 1, on the trestle 5, there is provided a stand 8 adapted to support a gripe for a rigid ball drop. A rigid ball drop-portion 7 formed at or near a distal end of the gripe is located off above the two buffer blocks 1A, 1B.

It should be noted that the strain waveform control apparatus according to the present invention is intended to perform an impact test on a printed circuit board in a state similar to that in which a newly developed printed circuit board is being actually packaged in a case where strengths of soldering and the like formed therein are tested. Therefore, a drop position of the rigid ball and initially set positions of the buffer blocks 1A, 1B change depending on a kind of the printed circuit board. Also, relative positions of the buffer blocks 1A, 1B with respect to the drop position of the rigid ball changes depending on a specimen.

Hereinafter, a measuring system (strain controlling system) of the impact test device as described above will be described with reference to FIG. 2. This measuring system is provided on a proper place of the printed circuit board 2 and comprises: a strain gauge 11 adapted to convert strains into electrical signals (e.g., voltage signals); a dynamic strain meter 12 adapted to detect dynamic strains based on the electrical signals from the strain gauge 11; and a personal computer 13 adapted to capture the measurement result from the dynamic stain meter 12 and analyze its strain waveforms, whereby, based on the analyzed strain waveforms, control signals are created and sent to the movable stages 3 such that a positional control to move the buffer blocks 1A, 1B is performed so as to obtain desired (or predetermined) strain waveforms as a result of an impact.

Figure 3:
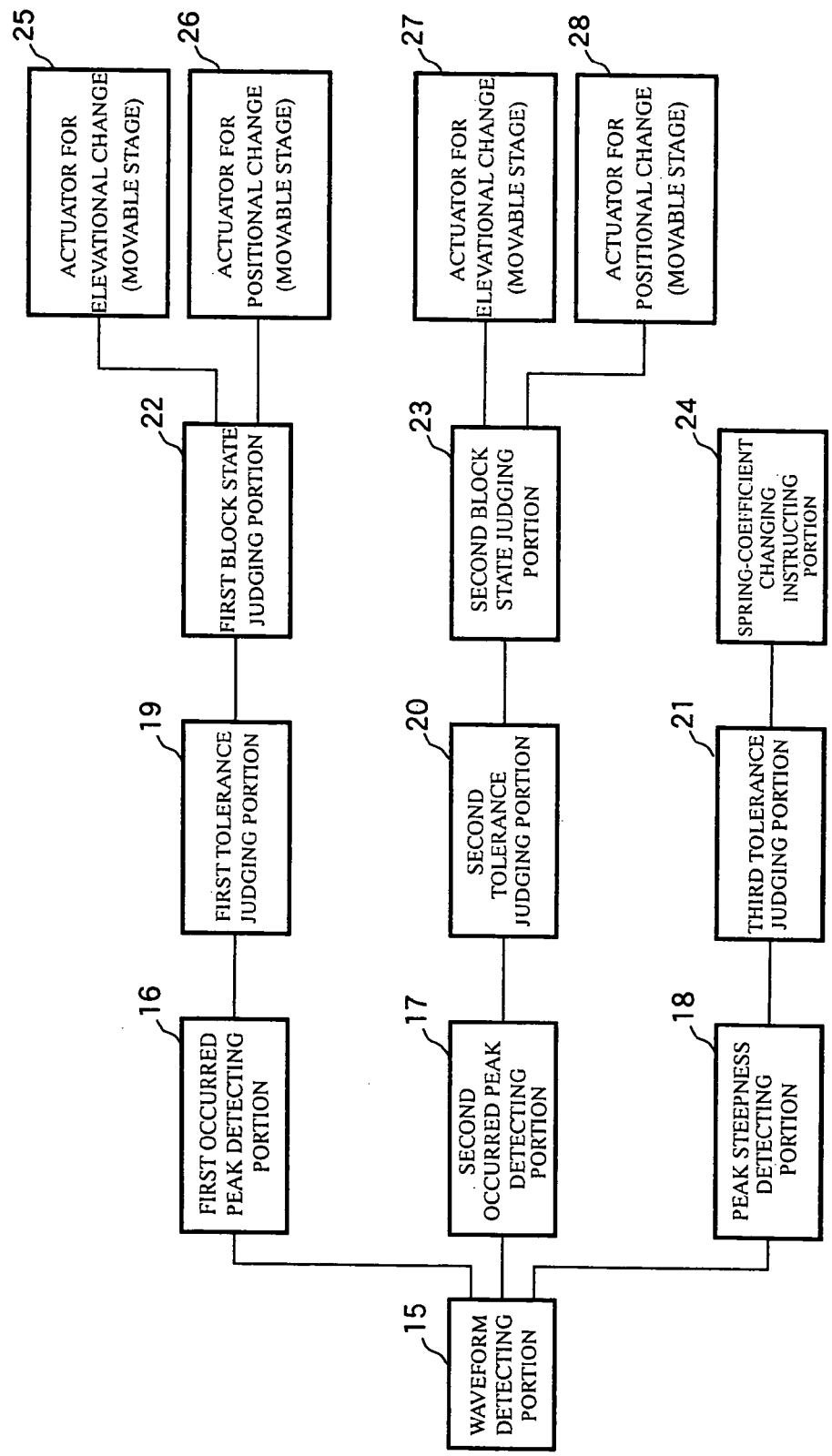
FIG. 3 is a functional block diagram of a strain waveform control apparatus according to the present invention.

FIG. 3 is a functional block diagram of the strain waveform control apparatus in the measuring system as described above. This strain waveform control apparatus comprises: a waveform detecting portion 15 adapted to detect strain waveforms; a first occurred peak detecting portion 16 adapted to detect a first peak (which is occurred first by means of an impact application and which protrudes from a surface opposite to a surface to which the impact is applied) occurred in response to the strain waveforms detected by the strain waveform detecting portion 15; a second occurred peak detecting portion 17 adapted to detect a second peak (which is occurred second by means of the impact application and which protrudes from a surface to which the impact is applied); and a peak steepness detecting portion 18 adapted to detect a peak steepness.

The strain waveform control apparatus further comprises: first, second and third tolerance judging portions 19, 20 and 21 adapted to judge whether respective objects to be detected (or respective detected objects) are within respective dedicated tolerances. In addition, the strain waveform control apparatus comprises: a first block state judging portion 22; an elevational change actuator for (the movable stage) 25; and a positional change actuator (the movable stage) 26. Whereupon, if the first occurred peak of the strain waveforms is judged not to be within a predetermined tolerance by the first tolerance judging portion 19, the first block state judging portion 22 judges a positional state of the main buffer block 1A provided on the (rear) opposite surface to the surface of the printed circuit board 2 to which the impact is applied. Then, based on the judgment output from the first block state judging portion 22, the elevational change actuator (the movable stage) 25 changes the elevation of the main buffer block 1A (a distance from the rear surface of the printed circuit board 2) and the positional change actuator (the movable stage) 26 changes the position of the main buffer block 1A in a direction parallel to the surface of the printed circuit board to which the impact is applied.

Also, if the second occurred peak of the strain waveform is judged not to be within a predetermined tolerance by the second tolerance judging portion 20, the second block state judging portion 23 judges a positional state of the main buffer block 1A provided on the (front) surface of the same as the surface of the printed circuit board 2 to which the impact is applied. Then, based on the judgment output from the second block state judging portion 23, the elevational change actuator (the movable stage) 27 changes the elevation of the main buffer block 1A (a distance from the front surface of the printed circuit board 2) and the positional change actuator (the movable stage) 28 changes the position of the main buffer block 1A in a direction parallel to the surface of the printed circuit board to which the impact is applied.

Furthermore, the strain waveform control apparatus comprises: a third tolerance judging portion 21 and a spring-coefficient changing instructing portion 24. If the steepness of the strain waveform (a rising of peak or a peak rising) is judged not to be within a predetermined tolerance by the third tolerance judging portion 21, the spring-coefficient changing instructing portion 24 outputs an instruction to change the spring-coefficient of the auxiliary buffer block 1B provided on the rear surface of the printed circuit board 2.

Figure 2:
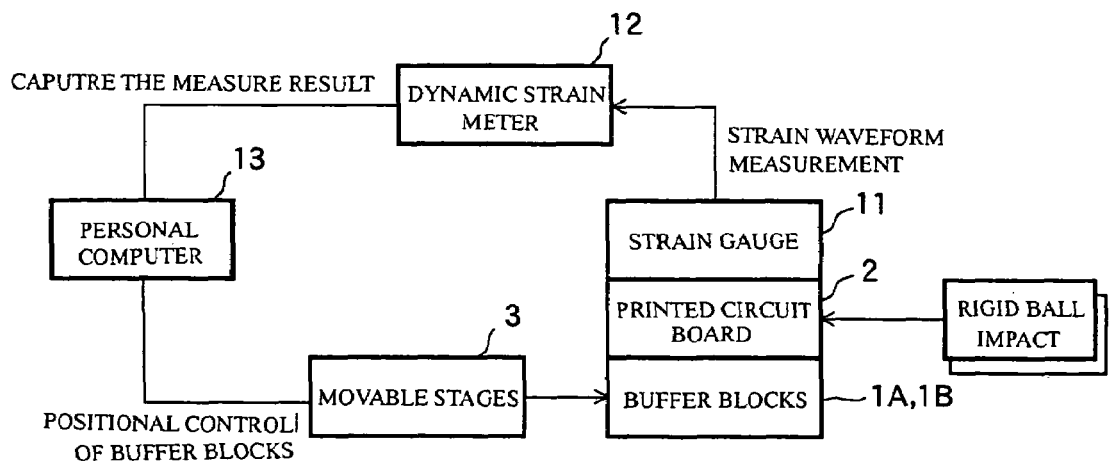
FIG. 2 is a schematic block diagram showing a strain waveform control system according to the present invention.

In the configuration as described above, the waveform detecting portion 15 is comprised of the strain gauge 11 and the dynamic strain meter 12 as shown in FIG. 2 while the personal computer 13 as shown in FIG. 2 includes the first, second and third judging portions 19, 20 and 21, the first and second block state judging portions 22 and 23, and the spring-coefficient changing instructing portion 24.

Figure 4:
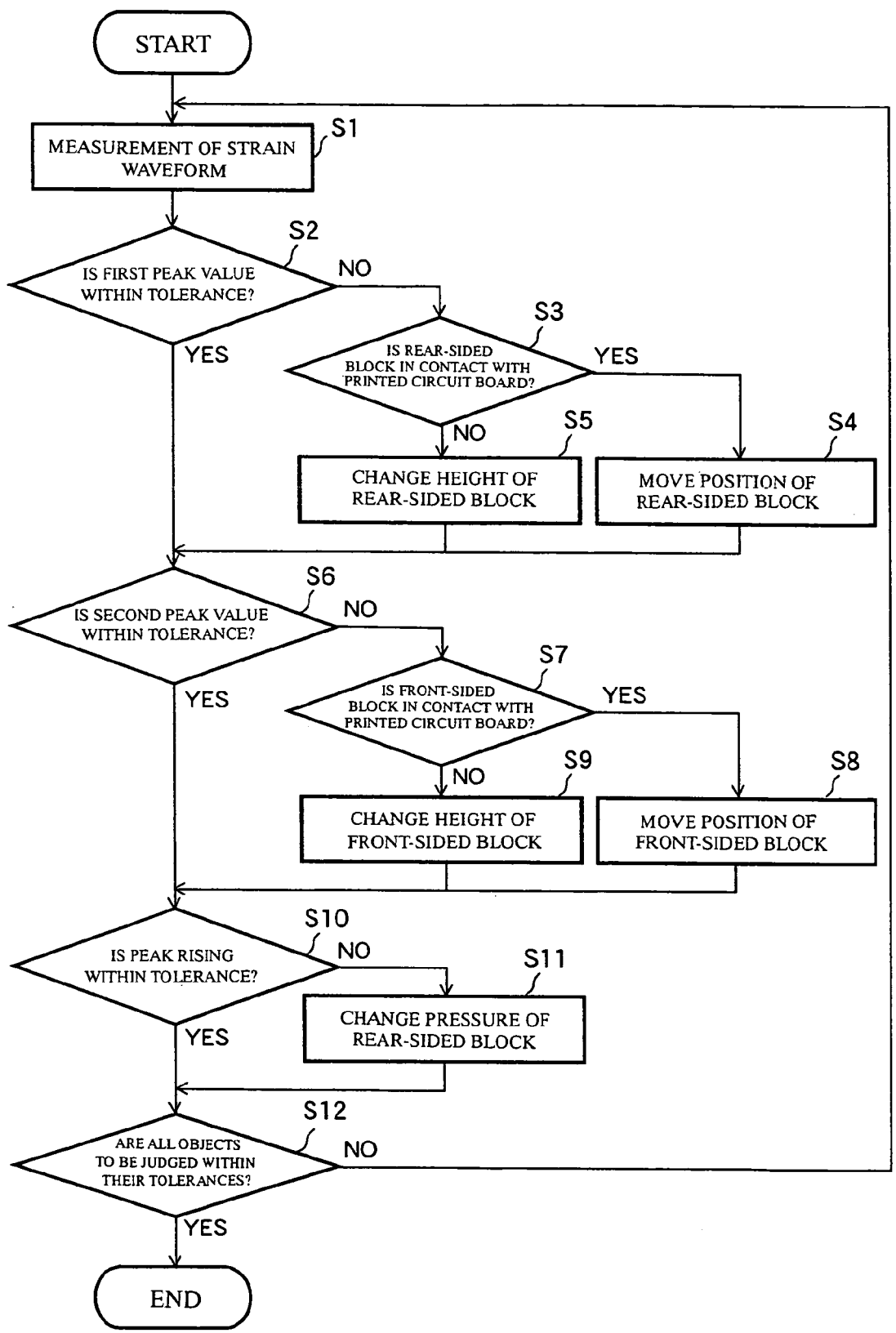
FIG. 4 is a flow chart showing processing steps of the strain waveform control apparatus.

Hereinafter, operations of the strain waveform control apparatus as configured above will be described with reference to a flow chart of FIG. 4.

Figure 6:
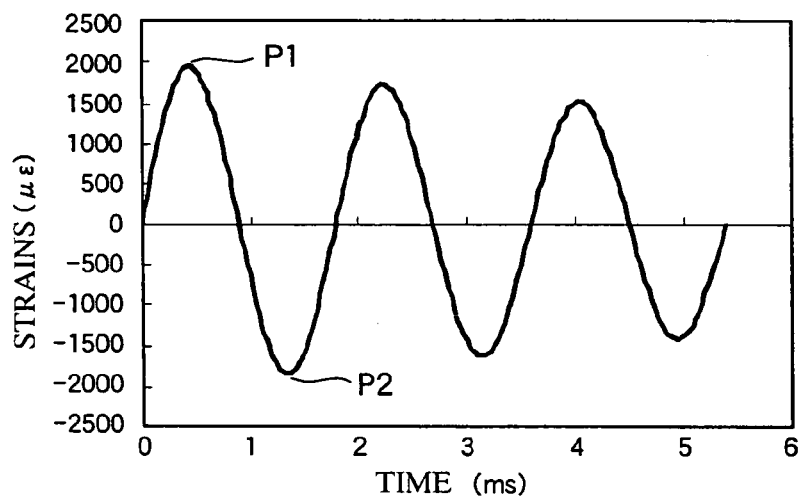
FIG. 6 is a time chart showing strain waveforms of a printed circuit board in a non-controlled state.

Firstly, the impact is applied to the surface of the printed circuit board 2 by the rigid ball drop, as a result of which strain waveforms are detected by the waveform detecting portion 15 to measure the strain waveforms (S1). Then, it is judged whether the value of a first occurred peak (P1 as shown in FIG. 6) of a first waveform from the strain waveforms is within a predetermined tolerance (S2). If the value is not within the predetermined tolerance (S2: N), then it is judged whether the main buffer block 1A disposed on the rear side of the printed circuit board 2 is in contact with the rear surface of the printed circuit board 2 (S3) when it is intended to lessen the peak of the strain waveform. If the main buffer block 1A is in contact with the rear surface of the printed circuit board 2 (S3: Y), then a positional movement of the main buffer block 1A is performed (changing the position of the main buffer block 1A in a direction parallel to the printed circuit board surface, e.g., to approximate a location at which the largest strain can be occurred) (S4). In addition, a judgment whether the main buffer block 1A is in contact with the printed circuit board 2 is performed based on a position at which the printed circuit board 2 is supported on the board setting part 4 and a height at which the main buffer block 1A is supported by the movable stage 3. On the other hand, if the main buffer block 1A is judged not to be in contact with the rear surface of the printed circuit board 2 (S3: N), then an elevation changing of the main buffer block 1A disposed on the rear side of the printed circuit board 2 is performed (changing the position of the main buffer block 1A in a direction perpendicular to the printed circuit board surface, e.g., to shorten a distance from the printed circuit board 2) (S5).

When the first occurred peak is judged in the step S2 to be within the predetermined tolerance (S2: Y) or after the processing of step S4 or S5, it is judged whether the value of a second occurred peak (P2 as shown in FIG. 6) of the strain waveforms is within a predetermined tolerance (S6). If the value is not within the predetermined tolerance (S6 :N), then it is judged whether the main buffer block 1A disposed on the front side of the printed circuit board 2 is in contact with the front surface of the printed circuit board 2 (S7). If the main buffer block 1A is in contact with the front surface of the printed circuit board 2 (S7: Y), then a positional movement of the main buffer block 1A is performed (changing the position of the main buffer block 1A in a direction parallel to the printed circuit board surface, e.g., to approximate a location at which the largest strain can be occurred) (S8). On the other hand, if the main buffer block 1A is judged not to be in contact with the front surface of the printed circuit board 2 (S7: N), then an elevation changing of the main buffer block 1A disposed on the front side of the printed circuit board 2 is performed (changing the position of the main buffer block 1A in a direction perpendicular to the printed circuit board surface, e.g., to shorten a distance from the printed circuit board 2) (S9).

When the second occurred peak is judged in the step S6 to be within a predetermined tolerance (S6: Y) or after the processing of step S9 or S8, it is judged whether its peak rising (a steepness of the first peak) is within a predetermined tolerance (S10). If the peak rising is not within the predetermined tolerance (S10: N), then the spring-coefficient of the auxiliary buffer block 1B on the rear side of the printed circuit board 2 (in the case of the auxiliary buffer block being absent, the spring-coefficient of only the main buffer block) or the spring-coefficient of the main buffer block in addition to the spring-coefficient of the auxiliary buffer block is changed in order to change a pressure on the rear surface of the printed circuit board 2 by the buffer block on the rear side thereof (When it is intended to enlarge the steepness, the spring-coefficient is changed to be enlarged. On the contrary, when it is intended to lessen the steepness, the spring-coefficient is changed to be lessened.) (S11). Incidentally, a supporting position for the auxiliary buffer block 1B may be arranged such that its contacting portion can be in contact with the printed circuit board surface or such that its contacting portion can be slightly spaced from the printed circuit board surface. This should be selected depending on a kind of a specimen. Also, in the case where there is no auxiliary buffer block 1B as shown in FIG. 10, the similar effect as described above is achieved by changing the spring-coefficient of the main buffer block 1A. However, if there is provided the auxiliary buffer block 1B as described above, the peak of the strain waveforms can be controlled in both of magnitude and steepness with higher freedom and readiness than the case where there is no auxiliary buffer block 1B. In particular, after the processing of the step S11 or when the peak rising is judged to be within the tolerance (S10: Y), the operations as described above will be repeated until all of objects to be judged (the first peak value, the second peak value and the peak rising) fall within their tolerances.

Figure 7:
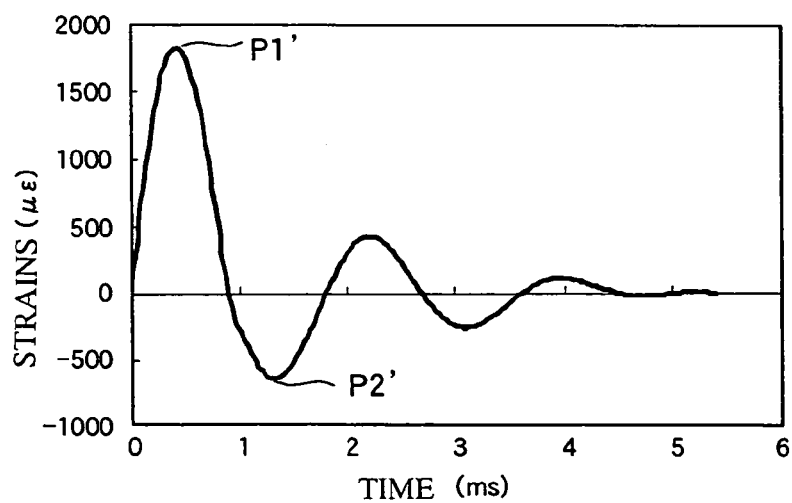
FIG. 7 is a time chart showing strain waveforms of the printed circuit board in a controlled state.

Meeting these operations, it is possible to control and change the original strain waveforms as shown in FIG. 6 into strain waveforms as shown in FIG. 7 by appropriately changing positions and/heights of the buffer blocks. In this case, strain waveforms are appropriately adjusted in peak and steepness such that a second waveform and thereafter are largely regulated in comparison with a first waveform.

Thus, in accordance with the present invention, it is possible to perform the impact test on a printed circuit board as if or on the condition that the printed circuit board is being built in the final product. In addition, amounts of elevational change and positional change of the buffer blocks and an amount of spring-coefficient change of the auxiliary buffer block 1B can experientially determined. For example, if there are provided printed circuit boards similar to previously-tested printed circuit boards, it is possible for the similar printed circuit boards to appropriately move the buffer blocks and/or change spring-coefficients thereof by utilizing a database storing therein the test results of the previously-tested printed circuit boards as experiential data.

Second Embodiment

Figure 8:
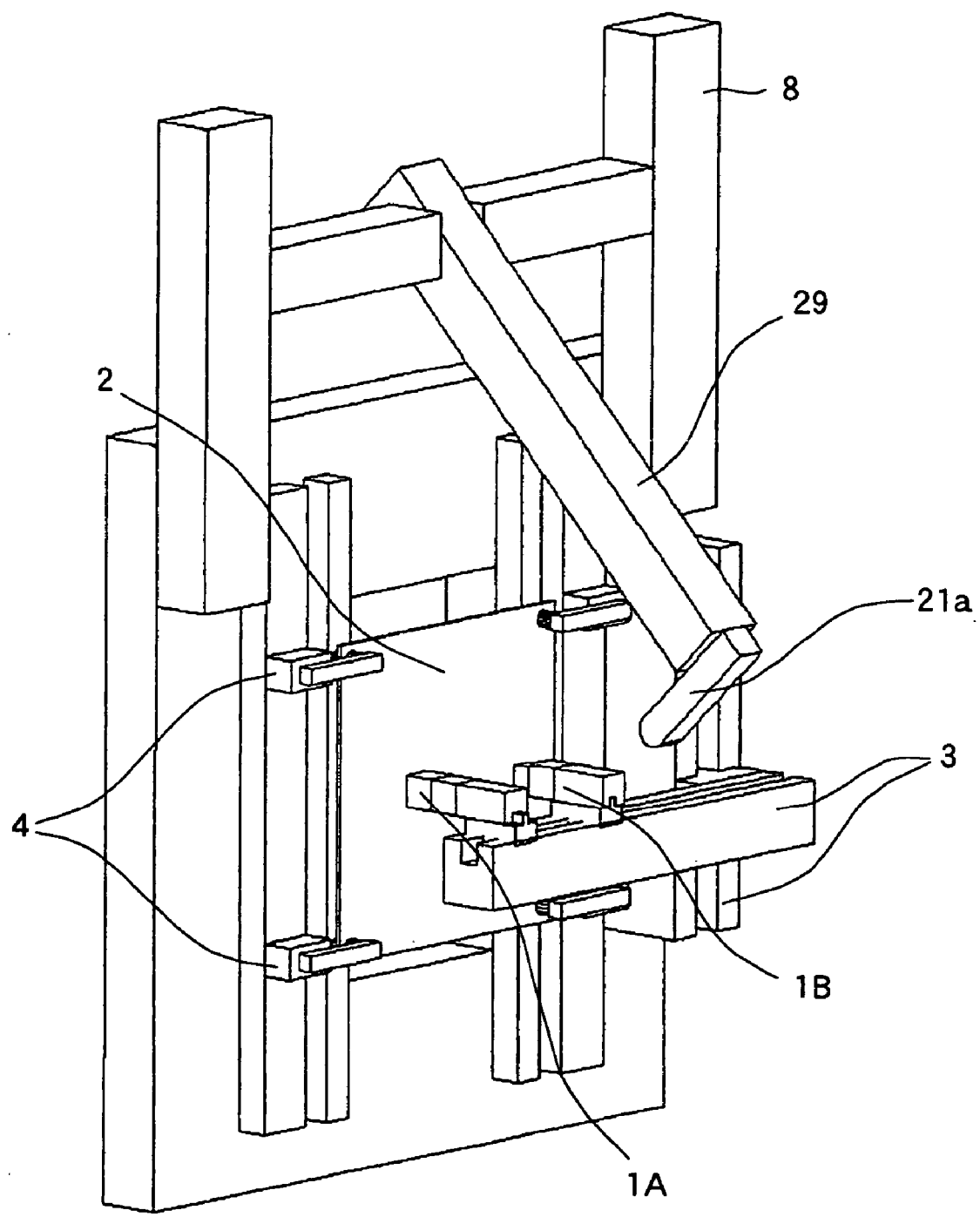
FIG. 8 is a perspective view showing a hammer-type impact test device according to a second embodiment of the present invention.

The first embodiment has been exemplified by using the rigid ball drop-type impact test device, but the present invention can be applicable to a hammer-type impact test device. FIG. 8 is a perspective view showing the hammer-type impact test device that is configured to stand a printed circuit board 2 uprightly on a trestle 5 and apply an impact to a surface of the uprightly stood printed circuit board 2 by a hammer 29 which drops swingingly like a pendulum. This hammer-type impact test device also comprises a main buffer block 1A and an auxiliary buffer block 1B movable in a direction parallel and in a direction perpendicular to the surface of the upright printed circuit board 2. Since these buffer blocks 1A, 1B are similar in actions or movements to those of the first embodiment, their explanations are omitted hereupon. The hammer 29 is swingably supported by a hammer supporting portion 8a spanning between stands 8 and comprise a striking portion 21a formed on its distal end.

Third Embodiment

Figure 9:
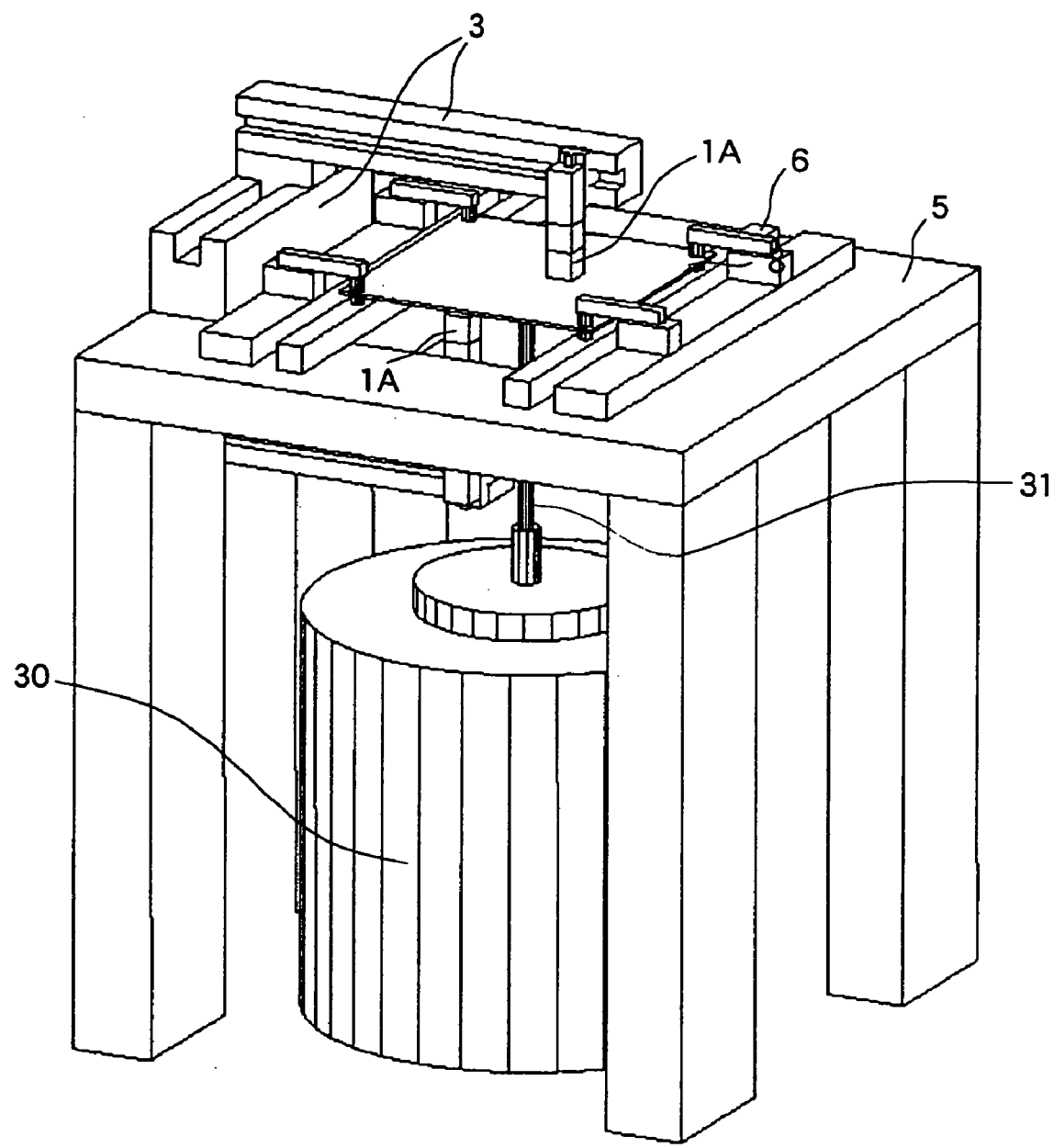
FIG. 9 is a perspective view showing a striking bar-type impact test device according to a third embodiment of the present invention.
Figure 11:
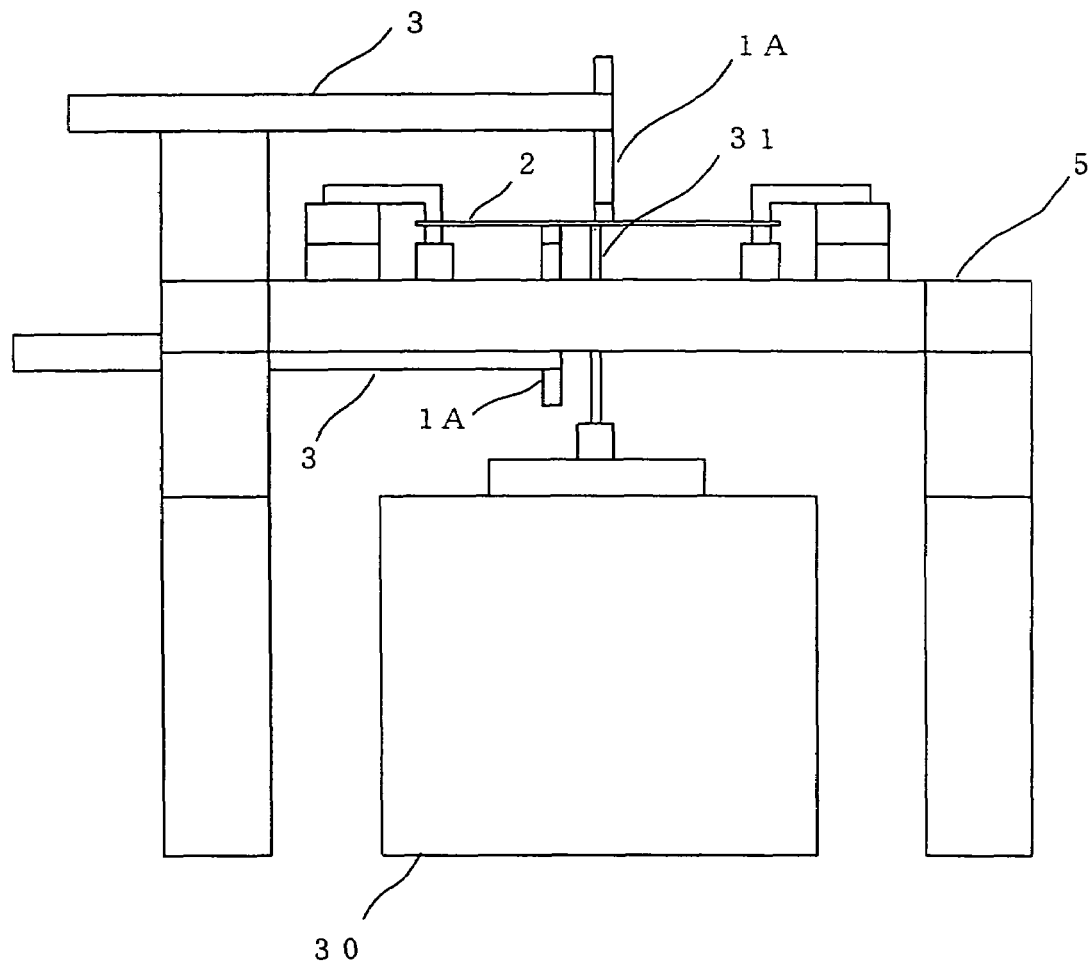
FIG. 11 is a simplified side view of the impact test device of FIG. 9.

In the third embodiment, the present invention is applied to a striking bar-type impact (vibration) test device (shaker). FIG. 9 is a perspective view showing the striking bar-type impact test device, and FIG. 11 is a schematic sectional view of the same device shown in FIG. 9. This impact test device is configured to horizontally support a printed circuit board 2 on a trestle 5 and apply an impact to a horizontally-provided surface of the printed circuit board 2 by a striking bar 31. In FIG. 9, only a main buffer block 1A is shown in a state in which it is supported by a movable stage 3. Needless to say, an auxiliary buffer block 1B, however, can be provided in addition to the main buffer block 1A, in a similar fashion to that as shown in FIG. 1.

As described above, various embodiments of the present invention have been explained. However, the present invention should not be limited to those embodiments and may be applicable to various technical fields without any departure from the spirit and scope of the invention. The embodiments as described above exemplify the printed circuit board as a specimen. However, other than the printed circuit boards, the present invention may be applicable to mobile equipments, PC and the like. In the embodiments as described above, it is intended to lessen the second peak in comparison with the first peak (changing the state as shown in FIG. 6 into the state as shown in FIG. 7). On the contrary, it is possible depending on a type of specimen to enlarge the second peak in comparison with the first peak (changing the state as shown in FIG. 7 into the state as shown in FIG. 6).

INDUSTRIAL APPLICABILITY

As described above, it is possible to control the strain waveforms obtained by applying the impact to the specimen according to the present invention. Especially, in the impact test, it is advantageously and effectively possible to perform the impact test on the specimen in a similar environment to a condition that or as if the specimen is actually being built in a box-like body, e.g., an outer casing, as the final product.

What is claimed is:

1. A strain waveform control apparatus, comprising:
 a specimen supporting portion adapted to support a specimen at a location of said specimen;

a strain generating portion adapted to generate strains by applying an impact to said specimen supported by said specimen supporting portion;

a strain waveform detecting portion adapted to detect strain waveforms of said specimen generated by said strain waveform generating portion;

at least one strain regulating member modifying and adjusting a strain waveform of said specimen and adapted to be contactably located on a place of a strain-causing surface of said specimen and moving in a direction parallel and perpendicular to the specimen; and a strain regulating member supporting portion adapted to movably support said at least one strain regulating member.

2. The strain waveform control apparatus as claimed in claim 1, further comprising a control portion adapted to drive said strain regulating member supporting portion to move said at least one strain regulating member adapted to change strain waveforms detected by said strain waveform detecting portion into predetermined waveforms.

3. The strain waveform control apparatus as claimed in claim 2, wherein said control portion is capable of controlling a positional relationship between said at least one strain regulating member and said specimen by driving said strain regulating member supporting portion so as to confine a first peak of strain waveforms generated by the impact within a predetermined range.

4. The strain waveform control apparatus as claimed in claim 2, wherein said control portion is capable of controlling a positional relationship between said at least one strain regulating member and said specimen by driving said strain regulating member supporting portion so as to confine a second peak of strain waveforms generated by the impact within a predetermined range.

5. The strain waveform control apparatus as claimed in claim 2, wherein said control portion is capable of controlling a positional relationship between said at least one strain regulating member and said specimen by driving said strain regulating member supporting portion so as to confine the maximum peak of strain waveforms generated by the impact within a predetermined range.

6. The strain waveform control apparatus as claimed in claim 2, wherein said control portion is capable of controlling a positional relationship between said at least one strain regulating member and said specimen by driving said strain regulating member supporting portion so as to confine the second largest peak of strain waveforms generated by the impact within a predetermined range.

7. The strain waveform control apparatus as claimed in claim 2, wherein said control portion is capable of controlling a positional relationship between said at least one strain regulating member and said specimen by driving said strain regulating member supporting portion so as to confine a steepness of each of strain waveforms generated by the impact within a predetermined range.

8. The strain waveform control apparatus as claimed in claim 2, wherein said control portion is capable of controlling a positional relationship between said at least one strain regulating member and said specimen by driving said strain regulating member supporting portion adapted to relatively modify/adjust first and second occurred waveforms of strain waveforms generated by the impact.

9. The strain waveform control apparatus as claimed in claim 2, wherein said strain regulating member supporting portion is capable of supporting said at least one strain regulating member so as to be movable in a direction perpendicular to an impacted surface of said specimen.

10. The strain waveform control apparatus as claimed in claim 2, wherein said strain regulating member supporting portion is capable of supporting said at least one strain regulating member so as to be movable in a direction parallel to an impacted surface of said specimen.

11. The strain waveform control apparatus as claimed in claim 1, wherein said strain regulating member supporting portion is capable of supporting said strain regulating member in a face-to-face relation to an impacted surface of said specimen and supporting the other strain regulating member in a face-to-face relation to the opposite surface of said specimen.

12. The strain waveform control apparatus as claimed in claim 1, wherein said at least one strain regulating member comprises: a first strain regulating member being effective in changing the magnitude of each of peaks of said strain waveforms; and a second strain regulating member being effective in changing a steepness of each of peaks of said strain waveforms.

13. The strain waveform control apparatus as claimed in claim 1, wherein said specimen comprises a printed circuit board implementing thereon an electrical circuit.

14. A strain waveform control apparatus, comprising:
a specimen supporting portion adapted to support a specimen at a location of said specimen;
a strain generating portion adapted to generate strains by applying an impact to said specimen supported by said specimen supporting portion;
a strain waveform detecting portion adapted to detect strain waveforms of said specimen generated by said strain waveform generating portion; and
a strain regulating member supporting portion adapted to movably support at least one strain regulating member to locate it contactably on and in a face-to-face relation to a place of a strain-causing surface of said specimen, said strain regulating member modifying and adjusting a strain waveform of said specimen and moving in a direction parallel and perpendicular to the specimen.

15. The strain waveform controlling apparatus as claimed in claim 14, further comprising a control portion adapted to drive said strain regulating member supporting portion to move said at least one strain regulating member so as to change strain waveforms detected by said strain waveform detecting portion into predetermined waveforms.

16. An impact test device comprising a strain waveform control apparatus to perform an impact test on a specimen, said strain waveform control apparatus comprising:
a specimen supporting portion adapted to support said specimen at a location of said specimen;
a strain generating portion adapted to generate strains by applying an impact to said specimen supported by said specimen supporting portion;
a strain waveform detecting portion adapted to detect strain waveforms of said specimen generated by said strain waveform generating portion;
at least one strain regulating member modifying and adjusting a strain waveform of said specimen and adapted to be contactably located on a place of a strain-causing surface of said specimen and moving in a direction parallel and perpendicular to the specimen; and
a strain regulating member supporting portion adapted to movably support said at least one strain regulating member.

17. A strain regulating member which can be supported by a strain regulating member supporting portion adapted to movably support said strain regulating member in a strain waveform control apparatus, said strain regulating member modifying and adjusting a strain waveform of said specimen and moving in a direction parallel and perpendicular to the specimen.

18. The strain regulating member as claimed in claim 17, having a predetermined elastic modulus.

19. The strain regulating member as claimed in claim 17, being composed of a rubber material.

20. The strain regulating member as claimed in claim 17, being composed of a spring material at its part where said strain regulating member is supported by said strain regulating member supporting portion and composed of a rubber material at its part where said strain regulating member can be in contact with a surface of a specimen.

21. The strain regulating member as claimed in claim 20, wherein said spring material part is independently exchangeable for others.

22. A strain waveform control apparatus equipped for an impact test device which is adapted to apply an impact to a specimen, comprising:
   a strain regulating member adapted to be contactably located on a place of a strain causing surface of said specimen and regulate strains generated on said specimen, said strain regulating member modifying and adjusting a strain waveform of said specimen; and
   a strain regulating member supporting/transporting mechanism attached to a location of the impact test device and adapted to support said strain regulating member so as to be movable in a direction perpendicular and in a direction parallel to said strain causing surface of said specimen.

23. The strain waveform control apparatus as claimed in claim 22, further comprising a control portion adapted to drive said strain regulating member supporting/transporting mechanism to control a position of said strain regulating member.

24. A method of controlling strain waveforms by using a strain waveform control apparatus adapted to support a specimen at a location of said specimen and to support a strain regulating member to locate it contactably on a place of said specimen, and further adapted to apply an impact to said specimen so as to generate strain waveforms and yet further adapted to control the strain waveforms, comprising the steps of:
   (a) detecting said strain waveforms generated by application of the impact to said specimen; and
   (b) changing a position of said strain regulating member based on said strain waveforms detected in the detecting said strain waveforms and controlling said strain waveforms to be converted into predetermined strain waveforms, said strain regulating member modifying and adjusting a strain waveform of said specimen and moving in a direction parallel and perpendicular to the specimen.

25. The method as claimed in claim 24, wherein the step (b) comprises moving said strain regulating member so as to confine a first peak of strain waveforms generated by the impact within a predetermined range.

26. The method as claimed in claim 24, wherein the step (b) comprises moving said strain regulating member so as to confine a second peak of strain waveforms generated by the impact within a predetermined range.

27. The method as claimed in claim 24, wherein the step (b) comprises moving said strain regulating member so as to confine the maximum peak of strain waveforms generated by the impact within a predetermined range.

28. The method as claimed in claim 24, wherein the step (b) comprises moving said strain regulating member so as to confine the second largest peak of strain waveforms generated by the impact within a predetermined range.

29. The method as claimed in claim 24, wherein the step (b) comprises moving said strain regulating member so as to confine a steepness of each of strain waveforms generated by the impact within a predetermined range.

30. The method as claimed in claim 24, wherein the step (b) comprises moving said strain regulating member adapted to relatively modify/adjust first and second occurred waveforms of strain waveforms generated by the impact.

31. In a strain waveform control apparatus adapted to support a specimen at a location of said specimen and to support a strain regulating member to be contactably located on a place of said specimen, and further adapted to apply an impact to said specimen so as to generate strain waveforms and yet further adapted to control the strain waveforms, a program adapted to cause a computer to execute a strain waveform control, comprising the steps of:
   (a) detecting said strain waveforms generated by application of the impact to said specimen; and
   (b) changing a position of said strain regulating member based on said strain waveforms detected in the detecting said strain waveforms and controlling said strain waveforms to be converted into predetermined strain waveforms, said strain regulating member modifying and adjusting a strain waveform of said specimen and moving in a direction parallel and perpendicular to the specimen.

32. The program as claimed in claim 31, wherein the step (b) comprises moving said strain regulating member so as to confine a first peak of strain waveforms generated by the impact within a predetermined range.

33. The program as claimed in claim 31, wherein the step (b) comprises moving said strain regulating member so as to confine a second peak of strain waveforms generated by the impact within a predetermined range.

34. The program as claimed in claim 31, wherein the step (b) comprises moving said strain regulating member so as to confine the maximum peak of strain waveforms generated by the impact within a predetermined range.

35. The program as claimed in claim 31, wherein the step (b) comprises moving said strain regulating member so as to confine the second largest peak of strain waveforms generated by the impact within a predetermined range.

36. The program as claimed in claim 31, wherein the step (b) comprises moving said strain regulating member so as to confine a steepness of each of strain waveforms generated by the impact within a predetermined range.

37. The program as claimed in claim 31, wherein the step (b) comprises changing a position of said strain regulating member adapted to relatively modify/adjust first and second occurred waveforms of strain waveforms generated by the impact.

38. A strain waveform control apparatus, comprising:
   a specimen supporting portion adapted to support a specimen at a location of said specimen;
   a strain generating portion adapted to generate strains by applying an impact to said specimen supported by said specimen supporting portion;
   a strain waveform detecting portion adapted to detect strain waveforms of said specimen generated by said strain waveform generating portion;

a main buffer block supported by a first movable stage corresponding to said main buffer block and coming into contact with and moving on a surface of the specimen corresponding to said main buffer block;

an auxiliary buffer block supported by a second movable stage corresponding to said auxiliary buffer block and adapted to come into contact with and move on a surface of the specimen corresponding to said auxiliary buffer block; and a strain regulating member supporting portion adapted to movably support said at least one of said main buffer block and said auxiliary block wherein said main buffer block and said auxiliary buffer block modify and adjust a strain waveform of the specimen and move in a direction parallel and perpendicular to the specimen.

39. A strain waveform control apparatus, comprising:

at least one strain regulating member modifying and adjusting a strain waveform of a specimen and contactably located on a strain-causing surface of said specimen and moving in a direction parallel and perpendicular to the specimen.

* * * * *